United States Patent [19]

Hobbs et al.

[11] Patent Number: 4,463,600
[45] Date of Patent: Aug. 7, 1984

[54] AUTOMATIC MEASUREMENT OF AREAS

[75] Inventors: Donald A. Hobbs, Solihull; Geoffrey W. Rowe, Birmingham, both of England

[73] Assignee: University of Birmingham, Birmingham, England

[21] Appl. No.: 295,790

[22] Filed: Aug. 24, 1981

[30] Foreign Application Priority Data

Sep. 23, 1980 [GB] United Kingdom ................. 8030640

[51] Int. Cl.³ .......................... G01N 3/48; G01N 3/42
[52] U.S. Cl. ....................................... 73/81; 356/378; 356/379
[58] Field of Search ............... 356/378, 379, 383, 384, 356/380, 387; 73/81, 82, 83

[56] References Cited

U.S. PATENT DOCUMENTS

| | | | |
|---|---|---|---|
| 3,754,436 | 8/1973 | Saxton | 73/81 |
| 3,947,130 | 3/1976 | Proctor | 356/383 X |
| 4,113,389 | 9/1978 | Kaye | 356/387 X |
| 4,159,522 | 6/1979 | Zanoni | 356/387 X |
| 4,255,966 | 3/1981 | Batie et al. | 73/81 |
| 4,275,966 | 6/1981 | Kleesattel | 356/378 |
| 4,324,335 | 4/1982 | Conway et al. | 356/380 X |
| 4,354,761 | 10/1982 | Jacoby | 356/378 |
| 4,372,152 | 2/1983 | Lewis et al. | 73/81 |

FOREIGN PATENT DOCUMENTS

| | | | |
|---|---|---|---|
| 1423636 | 3/1969 | Fed. Rep. of Germany | 356/380 |
| 2331124 | 5/1975 | Fed. Rep. of Germany | 73/81 |
| 577399 | 10/1977 | U.S.S.R. | 356/378 |

OTHER PUBLICATIONS

"Logic Circuitry and Vidicon Measure Displayed Areas", Feb. 1971, *Electronic Engineering*, vol. 43, No. 516, pp. 65-68, Myers et al.

*Primary Examiner*—S. Clement Swisher
*Assistant Examiner*—Tom Noland
*Attorney, Agent, or Firm*—Marshall, O'Toole, Gerstein, Murray & Bicknell

[57] ABSTRACT

The invention provides an apparatus and method for determining the hardness of a test piece supported in a predetermined position, by illuminating the test piece with an electromagnetic medium, receiving reflected medium in a television camera which provides a signal which varies in accordance with variations in intensity of the reflected medium, and electrically processing the signal to provide an output dependent upon the size of indentation which can be interpreted to determine the hardness of the test piece.

9 Claims, 4 Drawing Figures

AUTOMATIC MEASUREMENT OF AREAS

BACKGROUND OF THE INVENTION

1. Field of the Invention

This invention relates to an apparatus for determining size. More particularly, but not exclusively, the apparatus has been developed for automatically determining the area or dimensions of an indentation made by the indenter of a hardness tester such as a Vickers hardness tester, or the planar area, profile or silhouette area of an article.

Hardness testing is widely used in industry for the control of material quality and heat treatment. For information on a finer scale, for example on the depth of surface hardening or the distribution of subsurface tempering, micro hardness testing is used, in which the maximum dimension of the indentation may be 0.005 to 0.01 mm. Micro hardness studies are also important in investigations of failures due to cracks and fatique.

The principle of hardness and micro hardness testing is that an inverted pyramid, ball, or cone is pressed into the surface of a metal test piece and the size of the resulting impression is measured. This measurement is then converted to a numerical hardness value by comparing with tables.

In practice, the method is complex. All indenter movements must be carefully controlled for reproducability. The measurement procedure can be tedious and lead to eye strain, particularly when using a microscope with cursors for repetitive size measurements. These measurements frequently involve many separate measurements because many indentations have to be made in the test piece and the average size ascertained, because of the variability of the hardness of the material over the surface thereof.

SUMMARY OF THE INVENTION

The object of the invention is to provide a new or improved apparatus and method for determining size.

According to one aspect of the invention we provide an apparatus for determining the size of a test piece or of part of a test piece comprising means to support the test piece in a predetermined position, means to direct a medium onto the test piece, means responsive to said medium to provide a signal which varies in accordance with variations in intensity of said medium reflected from or transmitted from or past said test piece or part of the test piece, electrical processing means to process the signal to provide an output dependent upon the size of the test piece or the part of the test piece which can be interpreted to determine the size of the test piece, or part of the test piece.

According to a second aspect of the invention we provide a method of determining the size of the test piece or part of a test piece including the steps of directing a medium onto the test piece or part of a test piece, sensing the medium reflected from or transmitted from or past said test piece or part of the test piece with a medium responsive means which provides a signal which varies in accordance with variations in intensity of said reflected or transmitted medium to an electrical processing means, processing said signal with said electrical processing means to provide an output dependent upon the size of the test piece or part of the test piece, interpreting said output to determine the size of the test piece, or part of the test piece.

For example, the output may comprise a digital readout on a counter, or a readout from an apparatus programmed to provide an output only when the determined size of the workpiece or part of the workpiece is greater than a predetermined value.

The medium may be reflected from the test piece or part of the test piece, or from an area surrounding said test piece or part of a test piece.

The medium may be an electromagnetic, sonic or ultrasonic wave. Preferably however, the medium is an electromagnetic wave such as visible light in which case the medium responsive means may comprise for example, a photocell, light sensitive diode, or an array of photocells or light sensitive diodes, or a charge coupled device array but preferably, a television camera.

However the medium may comprise an electromagnetic wave of any frequency but whichever frequency is used, the medium responsive means must be chosen so as to be compatible therewith.

Where the medium is light and the medium responsive means comprises a television camera, a signal from the camera will comprise a sequence of frame signals, each frame signal containing information as to the dimensions and area of the test piece or part of the test piece, which may be displayed on a screen to provide an image of the test piece or part of the test piece.

Each frame signal is made up of a sequence of line signals which are horizontal when displayed on a screen, each line signal containing an element of said information.

It will be appreciated that where the light is light reflected from the test piece or part of the test piece, the image will appear on a screen, light, and the surrounding area black. However, where the light is reflected from the area surrounding the test piece or part of the test piece, the image will appear dark and the surrounding area light.

Each line signal for a single frame may be integrated by said electrical processing means to give an output dependent upon the total area of the test piece or part of the test piece.

Alternatively, where the test piece or part of the test piece is of regular configuration and in known orientation, the line signal corresponding to the largest horizontal dimension of the image may be selected by said electrical processing means and further processed to provide the output. For example where part of the test piece is a pyramidal shaped recess such as that produced by the indenter of a Vicker's hardness tester or a Knoop indenter, the diagonal will be of the largest horizontal dimension, and thus the line signal of the diagonal may be selected by the electrical processing means.

Thus, as the configuration of the test piece or part of the test piece is regular, the output will be dependent on the area of the test piece or part of the test piece.

The apparatus is particularly applicable for use in measuring the hardness of a material in which case the test piece may comprise a metal block having an indentation, the indentation having been caused by the indenter of the hardness tester.

The output will be dependent upon the area of the indentation and thus the hardness of the metal can be ascertained by comparing the size of the indentation with tables.

Alternatively, the electrical processing means may further comprise means programmed to convert the output which is dependent on the area of the indentation, into a hardness number on a known scale, for example the Vickers, Brinell, Rockwell or Myers hardness number, and to display said hardness number.

Preferably, the means which support the test piece are part of the hardness tester, the indenter of the hardness tester being a diamond of inverted pyramid configuration, or a ball or a cone.

Where the indenter is of inverted pyramid configuration such as in a Vicker's hardness tester or Knoop indenter, the indentation may be illuminated and the light reflected from one facet of the indentation only directed to said medium responsive means and not from the non-indented surface. Thus a test piece having a non-reflective e.g. rough surface can be examined since the medium is not required to be reflected from the rough surface but only from the smooth reflective surface produced by the indenter.

Thus the signal from the medium responsive means will contain information regarding the area of one quarter of the indentation. By suitable calibration, the electrical processing means may process the signal to give an output dependent upon the total area of the indentation.

Where the indenter comprises a ball such as in a Brinell hardness tester, the medium reflected from the area surrounding the indention may be passed to said medium responsive means to provide said signal, an obturating means being provided in the path of said medium, prior to the medium impinging upon said indentation to prevent medium falling on and being reflected from the bottom of the ball shaped indentation into said medium responsive means.

In the absence of such obturating means, light will be reflected from the bottom of the ball shaped indentation, into the medium responsive means. This will result in an inaccurate determination of area as the image of the indentation will appear as an annulus. The obturating means may comprise a circular patch of opaque material.

Preferably the medium responsive means, in use, is positioned or positionable at a location substantially coincident, relative to the indentation, with the support means of the indenter when the indenter made the indentation.

The apparatus may be used to determine hot or cold hardness of a metal object.

It has been found that the apparatus in accordance with the invention provides a more accurate determination of the hardness of the material than known methods. This is because the principle of measuring the area of an indentation is inherently more accurate than methods which measure only, for example, the length of a diagonal of a presumed square, which measurement ignores the curvature of the sides of the square which occurs due to material being displaced and "piled up" at the sides of the indentation, by the action of the indenter.

BRIEF DESCRIPTION OF THE DRAWINGS

The invention will now be described with the aid of the accompanying drawings in which.

DESCRIPTION OF THE PREFERRED EMBODIMENTS

Figure 1:
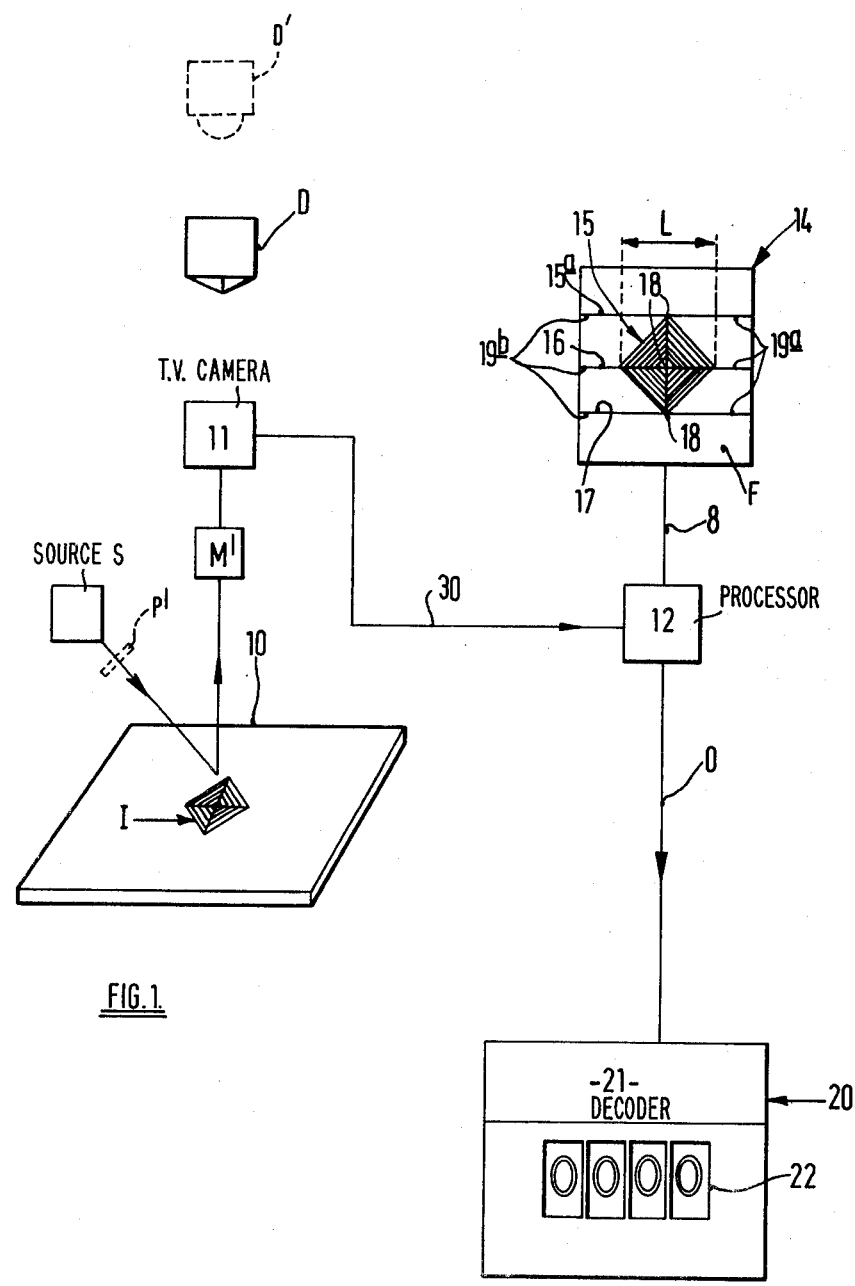
FIG. 1 is a schematic diagram showing the principles of operation of an apparatus in accordance with the invention.

Referring to FIG. 1, an apparatus in accordance with the invention comprises a Vickers hardness tester of known design, having an indenter D. A metal test piece 10 under investigation is placed in a position below the indenter D, which is made of daimond and of inverted pyramid configuration.

The indenter D is arranged to move vertically into contact with the metal test piece 10, a known force being applied thereto, for example ten kilogrammes.

After a predetermined period of time, for example ten seconds, the indenter D is raised and the test piece 10 is moved to a new position beneath the indenter and the indenting process is repeated.

This continues until an array of indentations I is produced.

In a conventional hardness tester, the indentations I would now be measured manually using a microscope M' provided with a cursor or cursors and a micrometer measuring device and the sizes of each of the indentations, individually ascertained. These are then converted to a Vickers hardness number using tables as is well known in the art, and the results averaged out to provide a single reading for the hardness of the test piece 10.

In the apparatus according to the invention however, instead of a micrometer measuring device the microscope M' is provided with a television camera 11.

The test piece 10 is illuminated with light from a source S and the light which is reflected from the area surrounding an indentation I is received by the television camera 11 after magnification by the lens system of microscope M'. The television camera 11 is positioned in substantially the same horizontal location, relative to the indentation I, as the indenter D when the indenter D made the indentation I.

It will be appreciated that at least some light from the indentation I may also be reflected into the camera 11 but this will be of less intensity than the light reflected from the area surrounding the indentation I.

Figure 2A:
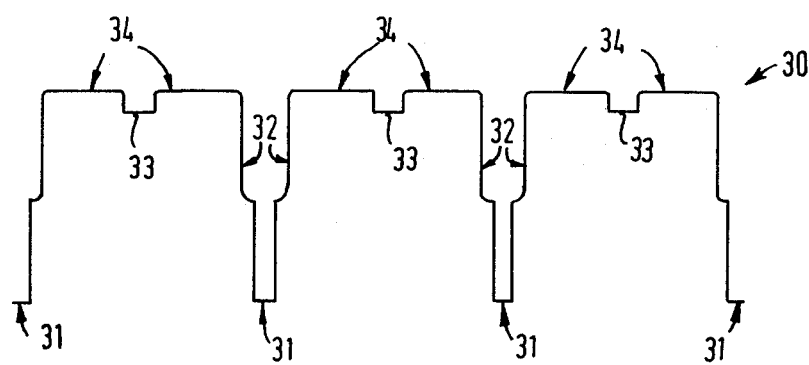
FIG. 2a is a schematic diagram of the video signal from the camera of FIG. 1.
Figure 2B:
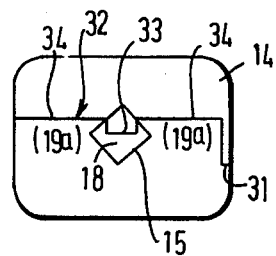
FIG. 2b is a schematic diagram of the way in which a line signal of FIG. 2a contains an element of information of an image.

A video signal from the camera 11, a small part of which is shown schematically in FIGS. 2a and 2b, is fed to an electrical processing means 12 which processes the signal to provide an output O which is dependent upon the area of the indentation I. The electrical processing means 12 also provides a signal 8 to a monitor screen 14 on which an image 15 of the indentation I is obtained. In the example shown, the indentation appears dark and the surrounding area light although the contrast could be reversed if required. The television camera 11 is of conventional black and white type and thus will not be further described, although if desired a colour television camera may be used. Referring to FIGS. 2a and 2b, the camera 11 provides a continuous signal 30 (FIG, 2a) comprising a sequence of frame signals which are made up of a sequence of line signals 32, each line signal 32 being separated from the remainder by pulses 31. Each frame signal contains a number of line signals, for example, 625 line signals, each signal containing information as to the complete image 15 and therefore, the size, of the indentation I.

Each line signal 32 contains an element of information regarding the image 15 of the indentation, part of the signal 32 containing information regarding the black part of the image (herein referred to as the black part of the signal) which is indicated at 33 in FIG. 2a and part of the signal 32 containing information regarding part of the signal 32 containing information regarding the white part of the image (herein referred to as the white part of the signal) which is indicated at 34 in FIG. 2a.

The image 15 of indentation I, and the relation of the image 15 to one line signal 32 of the signal shown in FIG. 2a, is diagrammatically shown in FIG. 2b.

When displayed on the screen 14, the white parts of the signal 34 appear at 19a, and the black part of the signal 33, at 18.

Some of the line signals 32 which make up the complete image 15 are also shown at 15a, 16 and 17 in FIG. 1. The output O from the electrical processing means 12 is fed to a readout device 20 as described hereinafter.

The electrical processing means 12 selects a single frame signal of the signal 30 from the camera 11 and analyses each line signal 32 of the frame individually. By suitable circuitry, the electrical processing means may alternatively analyse a sample only of the line signals if required.

The electrical processing means 12 adds together all the black parts of each line signal 32 for a single frame to provide the output O, which output O is thus dependent upon the total black area of the image 15 of the indentation I. The electrical processing means may comprise one or more integrated circuits or even a microprocessor as required.

The readout device 20 comprises a decoder 21 which decodes the output O for use in a digital display 22 of the device 20 and otherwise processes the ouput O to give a required readout.

In place of a digital display, the read out device 22 may comprise a further monitor screen for example, or a paper printout, a tape readout or any other readout.

The decoder 21 is programmed with, inter alia, an input of the indenting load and suitable calibrations of the apparatus, to convert the output O to a direct reading of the hardness of the test piece 10 on a known scale. For example, the display may give the Vickers hardness number or the Myers hardness number.

In an alternative embodiment, the electrical processing means 12 comprises a counter which counts pulses from an oscillator and is actuated by the black part 33 of each line signal 32 for a single frame.

Thus the total number of pulses from the oscillator counted in each line signal for a frame will be dependent upon the total black area of the indentation I. In this arrangement it will be appreciated that the greater the number of pulses provided per second by the oscillator, the greater the accuracy of the readout provided that the counter and associated circuitry are capable of reacting to the pulses.

In a still further embodiment, the electrical processing means may comprise a counter which counts pulses from an oscillator, the count for the black part of each line signal being compared with the highest count obtained from a previous line signal and the larger of the counts stored in a memory for further comparison. Thus the largest count corresponding to the line signal 32 having the largest black part will be stored in the memory, which count is dependent upon the largest horizontal dimension e.g. the diagonal length L of the image 15 of the indentation I.

As the indentation I is of regular configuration i.e. pyramidal and in the known particular orientation shown, the largest horizontal dimension L is dependent on the total area of the indentation which can be calculated therefrom, to provide output O.

However, this embodiment cannot be readily employed where the indenter and thus the indentation is in an unknown orientation or of irregular configuration, as the area of the indentation will not necessarily be dependent on the largest dimension L of the image 15.

The hardness tester is automated and coordinated with the camera 11, electrical processing means 12 and readout device 20 so that each indentation I of an array of indentations made by the indenter is examined in turn by the video camera 11.

The electrical processing means 12 may thus further comprise a circuit to average out the result obtained for each of the indentations of the array, to provide an output O averaged for all of the indentations.

Where the indenter is not of inverted pyramidal configuration, but a ball such as shown in dotted lines at D' in FIG. 1, it has been found that light is reflected from the bottom of the indentation of approximately the same intensity as light reflected from the surrounding area. Thus the determination of area is inaccurate, and the image 15 on screen 14 appears as an annulus. To overcome this problem, an obturating means such as an opaque circular patch shown in dotted lines at P' may be placed in the centre of the path of light from the source, to prevent light impinging upon the bottom of the indentation. The image thus appears as a circular disc.

Figure 3:
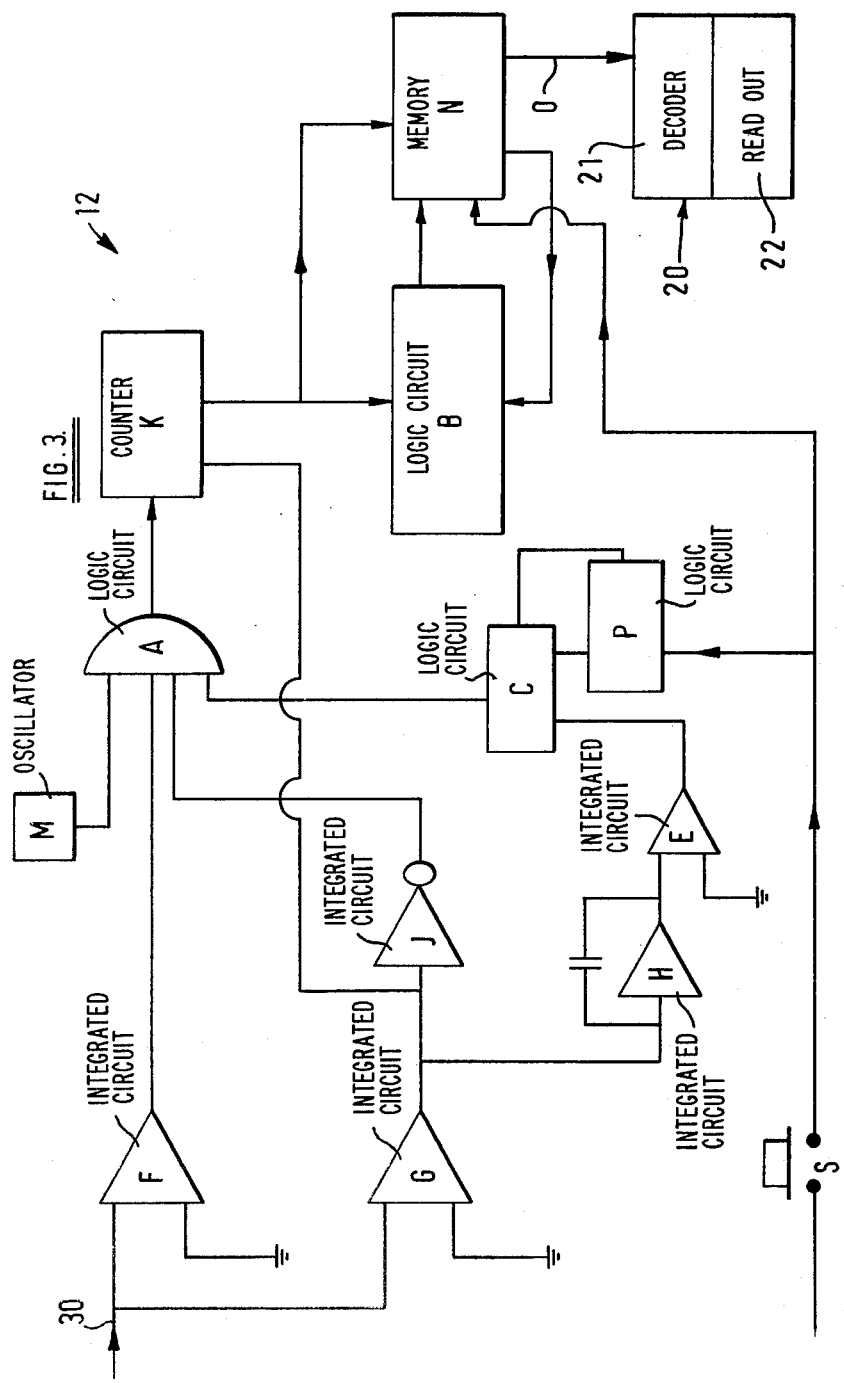
FIG. 3 is a schematic circuit diagram of an electrical processing means which may be used with the invention.

One example of an electrical processing means 12 which may be used with the arrangement described in FIG. 1, is shown in FIG. 3.

The means 12 comprise four logic circuits A to C, and P, and five integrated circuits E to J, a counter K, memory N, and oscillator M.

Circuit E selects a single frame signal in the continuous signal 30 from the camera 11 which signal is also independently detected by a circuit F. The individual line signals 32 for a single frame are sensed by a circuit G and the output from circuit G, which comprises line signals, is divided between integrated circuit H which integrates the signals to sum the total black parts 33 of each line signal 32 and an inverter amplifier J which feeds signals to logic circuit A which comprises a logic AND gate.

A start switch S is provided which directs a trigger signal to circuit P and memory N, thereby triggering P to accept the first frame, and opening the memory N. Logic C provides coincidence between trigger signal from the switch S on closure, and the frame selected by the circuit E.

When the black parts for each particular line signal have been summed by integrator H, a logic AND gate A causes and counter K to count a number of pulses from an oscillator M, which comprises a five megahertz clock, for a time corresponding to the length of the summed black parts of the line signal 32. The count is then passed to logic circuit B which comprises a comparator and this compares the count with a previous count for a previous line signal, which is stored in memory N. Whichever count is the greater is retained in the memory N.

When all the line signals for a selected frame have been processed, the memory N will contain a count corresponding to the line signal 32 of the selected frame having the greatest black parts 33, which will correspond to the largest horizontal dimension of the image 15 of the indentation I which appears on the screen 14.

As the indentation I is in known orientation and as the indenter D is of regular configuration, the count will thus be dependent upon the total area of the indentation I and by suitable calibration of the apparatus, and calculation, the total area of the indentation I can be ascertained, if desired.

The output O from the memory N which is dependent upon the total area of the indentation I is then fed to a decoder 21 which decodes the output O and converts it for use with a digital readout 22. The decoder 21 is programmed to convert the count to a hardness number on a known scale such as the Vickers or Myers hardness number.

In an alternative arrangement, the indentation I is illuminated, and the camera 11 positioned so that the light reflected from one facet of the diamond shaped indentation only will enter the camera 11. Thus the image of the facet will appear light on the monitor screen and the surrounding area will appear dark.

Similar electrical processing means as those described above may be employed but they need to be adapted to be responsive to the white part of the line signals and not the black part. Further, the electrical processing means will need to multiply the area determined, by four, as the indentation has four facets, although the area of only one facet is measured.

The invention has been described as being used to determine the size of an indentation in a hardness testing apparatus and is also useful in microhardness testing.

Although the medium which is directed onto the test piece or part of the test piece has been described as being light, if desired, an electromagnetic wave of any desired frequency may be used.

We claim:

1. A hardness testing apparatus for determining the hardness of a test piece comprising:
    means for supporting the test piece in a predetermined position;
    indenter means for making an indentation in the test piece;
    means for directing an electromagnetic medium onto the test piece;
    television camera means responsive to said medium for providing a signal which varies in accordance with variations in intensity of said medium reflected from said test piece;
    electrical processing means for processing the signal to provide an output dependent upon the area of the indentation in the test piece; and
    means for interpreting said output to determine the hardness of the test piece in which the indentation is made.

2. An apparatus according to claim 1 wherein the electromagnetic medium is visible light, further including a television screen on which an image of the indentation is displayed.

3. An apparatus according to claim 2, wherein the indentation is of regular configuration and in known orientation, and the line signal in the signal from the television camera corresponding to the largest horizontal dimension of the image is selected by said electrical processing means and is further processed to provide the output.

4. An apparatus according to claim 1 wherein the electrical processing means integrates each line signal in the signal from the television camera for a single frame to give an output dependent upon the area of the indentation and hence the hardness of the test piece.

5. An apparatus according to claim 1 wherein the electrical processing means further comprises means programmed to convert the output which is dependent on the area of the indentation into a hardness number on a known scale and to display said hardness number.

6. An apparatus according to claim 1 wherein the indenter is of inverted pyramid configuration, and the medium reflected only from one facet of the indentation and not from the non-indented surface is directed to said television camera means, the electrical processing means processing the signal to give an output dependent upon the total area of the indentation.

7. An apparatus according to claim 1 wherein the indenter comprises a ball and the medium which is reflected from the area surrounding the indentation passes to said television camera to provide said signal, further including an obturating means provided in the path of said medium prior to impinging upon the test piece, to prevent medium from being reflected from the bottom of the ball shaped indentation into said television camera means.

8. An apparatus according to claim 1 wherein the television camera means, in use, is positionable at a location substantially coincident, relative to the indentation, with the location of the indenter means when the indenter means made the indentation.

9. A method of determining the hardness of a test piece, including the steps of:
    making an indentation in the test piece;
    directing an electromagnetic medium onto the test piece;
    sensing the medium reflected from said test piece with a television camera means to provide a signal which varies in accordance with variations in intensity of said reflected medium, processing said signal with electrical processing means to provide an output dependent upon the area of the indentation in the test piece; and
    interpreting said output to determine the hardness of the test piece.

* * * * *